(12) United States Patent
Sforza

(10) Patent No.: US 10,398,813 B2
(45) Date of Patent: Sep. 3, 2019

(54) HARVESTING CANNULA

(71) Applicant: Marcos Sforza, Belgrade (RS)

(72) Inventor: Marcos Sforza, Belgrade (RS)

(*) Notice: Subject to any disclaimer, the term of this patent is extended or adjusted under 35 U.S.C. 154(b) by 260 days.

(21) Appl. No.: 15/054,364

(22) Filed: Feb. 26, 2016

(65) Prior Publication Data
US 2017/0021066 A1 Jan. 26, 2017

Related U.S. Application Data

(60) Provisional application No. 62/121,917, filed on Feb. 27, 2015.

(51) Int. Cl.
*A61M 1/00* (2006.01)
(52) U.S. Cl.
CPC ......... *A61M 1/008* (2013.01); *A61M 2202/08* (2013.01)
(58) Field of Classification Search
CPC .............................. A61M 1/008; A61M 25/00
USPC .............................................. 604/22, 35, 264
See application file for complete search history.

(56) References Cited

U.S. PATENT DOCUMENTS

| | | | | | |
|---|---|---|---|---|---|
| 3,924,617 | A * | 12/1975 | Ferro | ..................... | A61M 1/008 604/411 |
| 5,287,857 | A * | 2/1994 | Mann | ................ | A61M 25/0041 600/566 |
| 5,320,110 | A * | 6/1994 | Wang | ................. | A61B 10/0275 600/566 |
| 5,674,237 | A * | 10/1997 | Ott | ..................... | A61B 17/3496 604/264 |
| 5,725,495 | A * | 3/1998 | Strukel | ............... | A61M 1/0043 604/22 |
| 5,817,050 | A * | 10/1998 | Klein | .................... | A61M 1/008 604/35 |
| 6,020,196 | A * | 2/2000 | Hu | .......................... | A61M 1/00 435/283.1 |
| 6,027,514 | A * | 2/2000 | Stine | .............. | A61B 17/320783 600/564 |
| 6,030,400 | A * | 2/2000 | Johnson | ............. | A61B 10/0233 606/167 |
| 7,056,315 | B2 * | 6/2006 | Gonon | ............. | A61B 17/32037 604/164.11 |
| 8,057,403 | B2 * | 11/2011 | Ireland | ............... | A61B 10/0275 600/562 |
| 8,267,891 | B2 * | 9/2012 | Dimalanta | ............ | A61M 1/008 604/118 |
| 8,702,784 | B2 * | 4/2014 | Weisman | .................. | A61F 2/95 604/264 |
| 2002/0169469 | A1 * | 11/2002 | Klein | ............. | A61B 17/320783 606/167 |
| 2002/0188280 | A1 * | 12/2002 | Nguyen | ......... | A61B 17/320016 604/542 |

(Continued)

OTHER PUBLICATIONS

Definition of "port" by Merriam-Webster, printed from https://www.merriam-webster.com/dictionary/port, Apr. 20, 2018.*

(Continued)

*Primary Examiner* — Susan S Su
(74) *Attorney, Agent, or Firm* — Stroock & Stroock & Lavan LLP

(57) ABSTRACT

A harvesting cannula, including a plurality of ports configured and positioned to improve performance as compared to existing harvesting devices, according to various embodiments, is described herein.

18 Claims, 5 Drawing Sheets

(56) References Cited

U.S. PATENT DOCUMENTS

| | | | |
|---|---|---|---|
| 2003/0135219 A1* | 7/2003 | Salyer | A61B 17/1666 606/81 |
| 2004/0267265 A1* | 12/2004 | Kyle | A61B 17/7098 606/304 |
| 2008/0167613 A1* | 7/2008 | Khouri | A61M 1/0009 604/119 |
| 2009/0054805 A1* | 2/2009 | Boyle, Jr. | A61B 10/0266 600/564 |
| 2009/0069831 A1* | 3/2009 | Miller | A61B 17/32 606/171 |
| 2009/0234378 A1* | 9/2009 | Escudero | A61B 17/320758 606/180 |
| 2011/0282337 A1* | 11/2011 | Hall | A61B 10/0266 606/33 |
| 2012/0027804 A1* | 2/2012 | Odermatt | A61B 17/06166 424/400 |
| 2013/0072912 A1* | 3/2013 | Del Vecchio | A61M 39/00 604/542 |
| 2013/0138053 A1* | 5/2013 | Shippert | A61M 5/00 604/272 |
| 2013/0253649 A1* | 9/2013 | Davis | A61B 17/1615 623/17.16 |
| 2014/0276741 A1* | 9/2014 | McKay | A61B 18/148 606/33 |
| 2015/0297810 A1* | 10/2015 | Rubin | A61M 1/008 604/542 |
| 2015/0335485 A1* | 11/2015 | Rieger | A61F 9/00763 606/171 |
| 2016/0066929 A1* | 3/2016 | Russo | A61B 17/1635 606/83 |
| 2016/0183962 A1* | 6/2016 | Spitz | A61B 17/32002 600/104 |
| 2016/0367784 A1* | 12/2016 | Wells | A61M 25/002 |

OTHER PUBLICATIONS

Dr. Klein, "Chapter 27: Microcannulas," Liposuction Textbook, obtained from https://web.archive.org/, Jan. 17, 2013. (Year: 2013).*

* cited by examiner

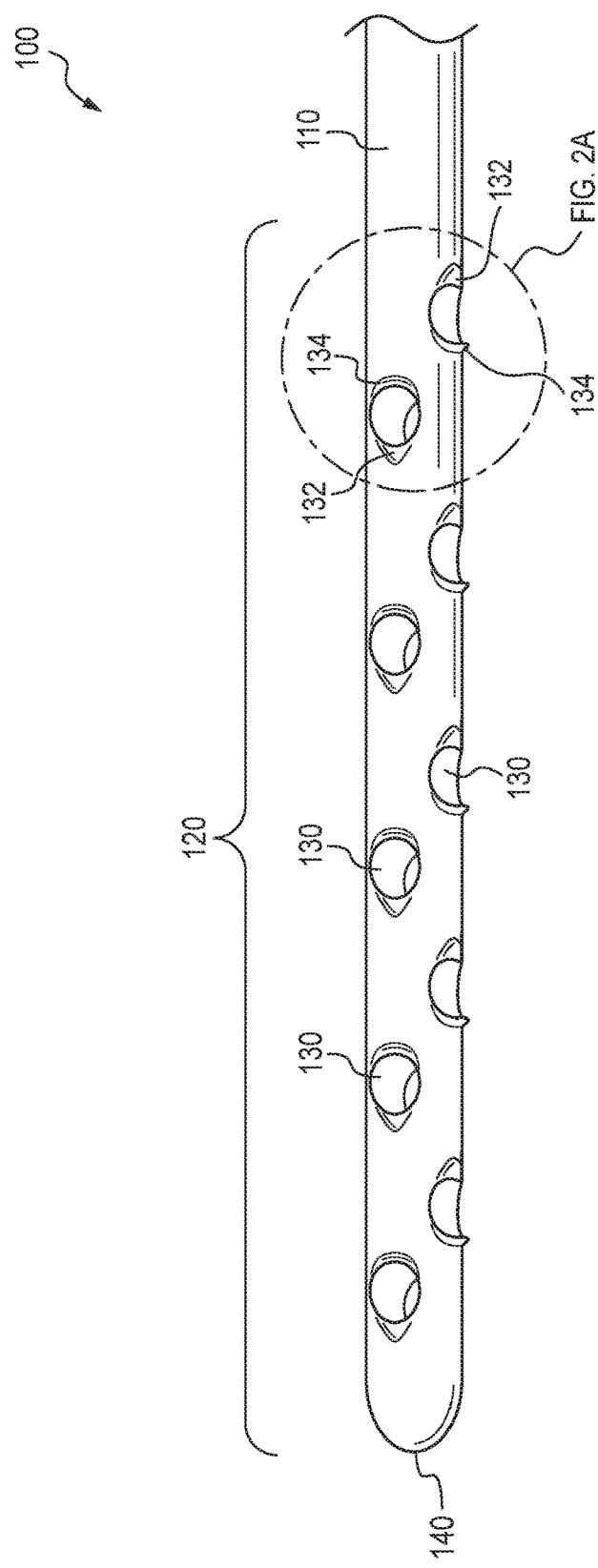

HARVESTING CANNULA

RELATED APPLICATIONS

This application claims the benefit of, and priority to, U.S. Provisional Application No. 62/121,917, filed Feb. 27, 2015, entitled "Harvesting Cannula," which is incorporated herein by reference in its entirety.

BACKGROUND

Use of a cannula, for example, to harvest fat from a patient, can be traumatic and/or inefficient. Improved harvesting cannulas that can overcome these drawbacks and/or provide other advantages are needed in the art.

SUMMARY

The present invention provides, in various embodiments, a harvesting cannula including a plurality of ports configured and positioned to improve performance as compared to existing harvesting devices.

In some embodiments, the invention provides a harvesting cannula comprising a hollow elongated stem, an open proximal end, and a closed distal end, wherein a distal portion of the stem comprises a plurality of barbed and beveled ports, each port comprising a hole having a beveled portion at one end and an elevated portion opposite thereto.

In some embodiments, each beveled portion comprises a 60 degree machined cutting edge. In some embodiments, each elevated portion has an extension of about 1 mm.

In some embodiments, the barbed and beveled ports each comprise a hole of about 1 mm in diameter.

In some embodiments, the barbed and beveled ports each comprise a hole of about 1.2 mm in diameter.

In some embodiments, the barbed and beveled ports are distributed in lines along the length of the stem, each line staggered and inverted in orientation relative to the lines adjacent thereto.

In some embodiments, the barbed and beveled ports are distributed in four lines of five ports each.

In some embodiments, the stem has a length between about 10 cm and about 45 cm.

In some embodiments, the stem has a length of about 35 cm.

In some embodiments, the stem is 13 gauge with an outer diameter of about 2.4 mm and an inner diameter of about 1.96 mm In some embodiments, the stem is 11 gauge with an outer diameter of about 3.0 mm and an inner diameter of about 2.39 mm.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of the preferred embodiments of the application, will be better understood when read in conjunction with the appended drawings. For the purposes of illustrating the device of the present application, there are shown in the drawings preferred embodiments. It should be understood, however, that the application is not limited to the precise arrangements and instrumentalities shown. In the drawings:

FIG. 1A shows a side view of the distal portion of a cannula according to some embodiments of the invention.

DETAILED DESCRIPTION

Autologous fat grafting is useful for a variety of surgical procedures. Many surgeons largely accept the use of fat as a natural filler. Anti-inflammatory properties of fat-derived skin cells following transfer to other areas can also be beneficial. However, existing devices for harvesting fat can be traumatic and/or inefficient.

The present invention provides, in various embodiments, an improved harvesting cannula. In preferred embodiments, the cannula is a microport harvester that can provide, for example, improved harvesting speed, as compared to existing devices. Cannulas according to the present invention are particularly suitable for harvesting fat (adipose tissue) in the context of surgical procedures such as fat transfer and/or liposculpture; however, the invention is not limited to such uses.

Figure 1B:
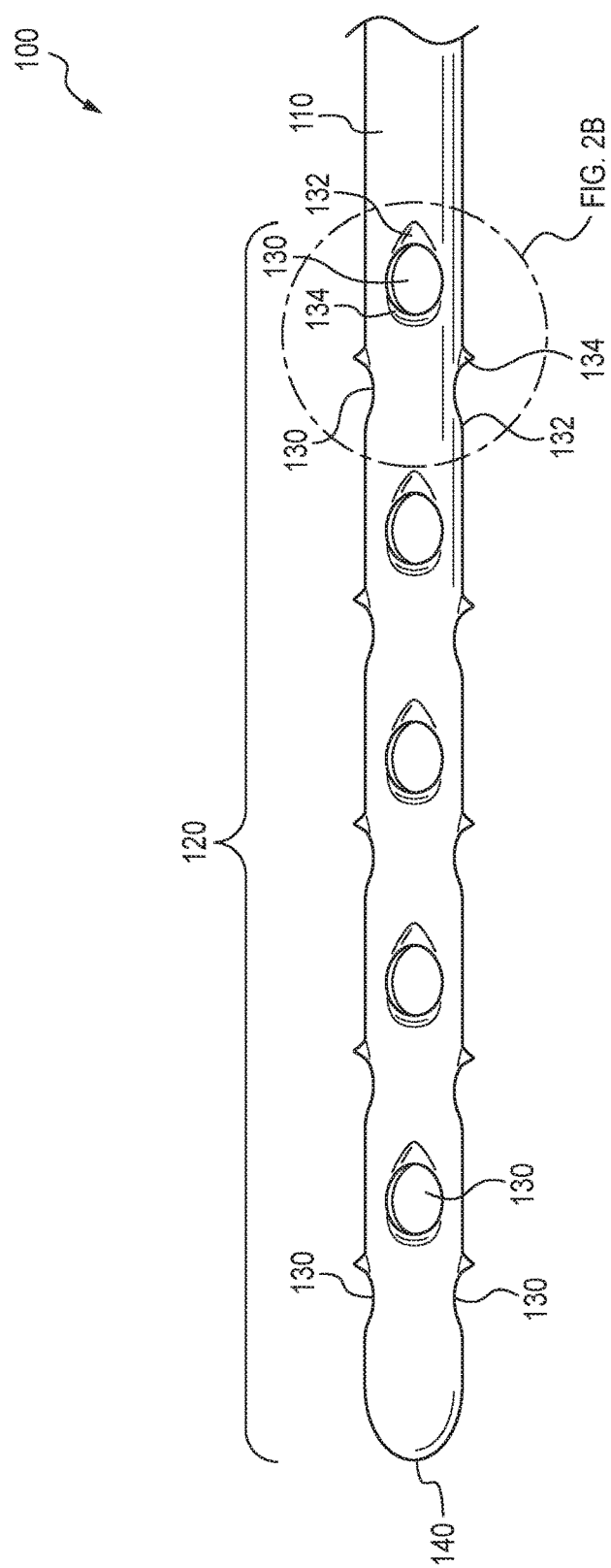
FIG. 1B shows an alternate side view of the distal portion of the cannula, wherein the cannula is rotated clockwise with respect to the view of FIG. 1A.

With reference to FIGS. 1A, 1B, 2A, 2B, and 3, in various embodiments, a cannula 100 is provided, which comprises an extended hollow rod (stem) 110 with a distal portion 120 having a plurality of specially-configured holes 130 and a closed distal tip 140. The distal tip 140 may be rounded (as shown), or may have another shape (conical, flat end, etc.). As shown in FIGS. 1A and 1B, in preferred embodiments, the specially-configured holes 130 comprise barbed and beveled ports, aligned so as to alternate in position and orientation along the distal portion 120 of the cannula 100, as described in further detail below.

In some embodiments, each specially-configured hole 130 comprises a beveled portion 132 at one end. As shown, for example, in FIGS. 2A and 2B, in certain preferred embodiments, each beveled portion 132 comprises a 60 degree machined cutting edges. In alternate embodiments, other types of beveled edges may be used.

Figure 2A:
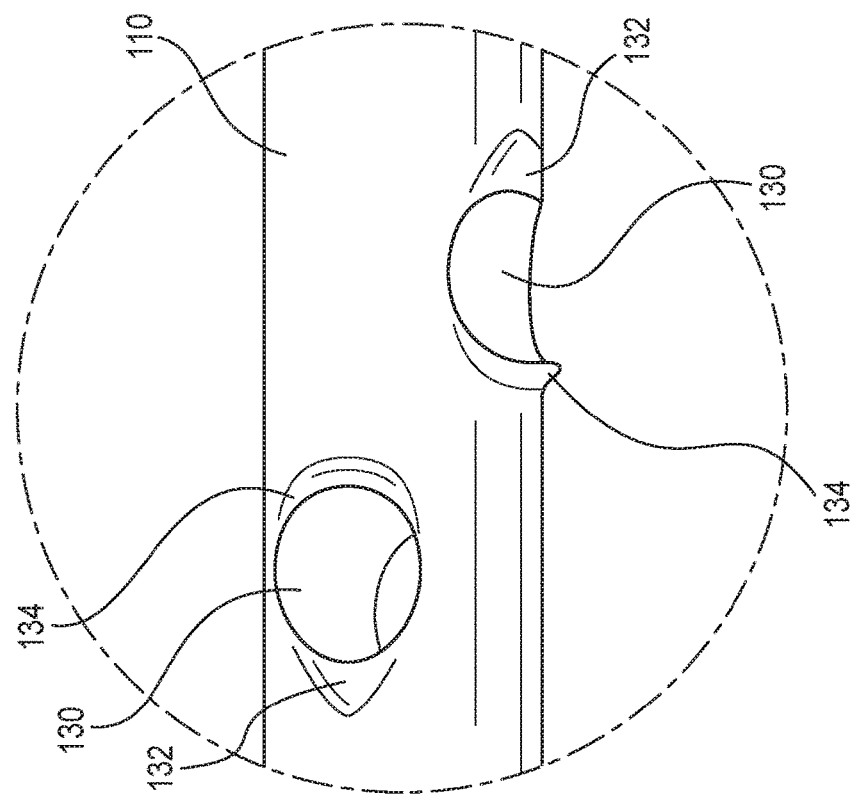
FIG. 2A shows a close-up view of the cannula of FIG. 1A, with exemplary features of the ports labeled.
Figure 2B:
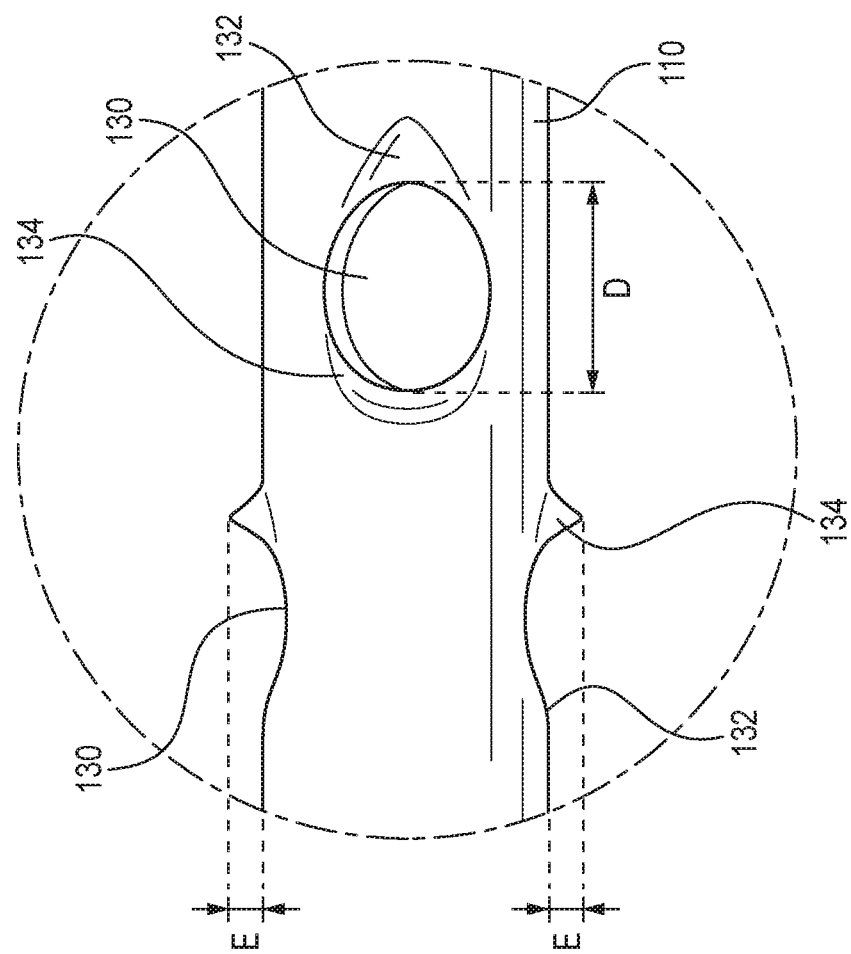
FIG. 2B shows a close-up view of the cannula of FIG. 1B, with exemplary features of the ports labeled.

Each specially-configured hole 130 may also comprise an elevated portion 134 at the other end, opposite the beveled edge 132. As shown in FIGS. 2A and 2B, in certain preferred embodiments, the elevated portion 134 comprises a projection having an extension (E) of about 1 mm beyond the outer surface of the cannula stem 110 and has a curved, brim-like exterior shape. In alternate embodiments, this elevation and/or shape may vary.

As shown in FIGS. 1A and 1B, in some embodiments, the cannula 100 includes twenty (20) specially-configured holes 130 distributed in four lines of five holes each. The number of holes and/or number of lines may vary in alternate embodiments. However, it is preferred that the lines are positioned in an alternating offset pattern (staggered), so that the specially-configured holes 130 are distributed around and along the length of the distal portion 120 of the cannula 100, for example, as shown in FIG. 1A.

In addition, it is particularly preferred that the lines of specially-configured holes 130 are inverted relative to one another, to provide bidirectional aspiration. Thus, as shown, for example, in FIG. 2A, where one line (at top) comprises holes 130 each oriented so that the beveled portion 132 is toward the distal end 140 of the cannula 100 and the elevated portion 134 is toward the proximal end 150, the adjacent line (at bottom) comprises holes 130 each oriented so that the elevated portion 134 is toward the distal end 140 of the cannula 100 and the beveled portion 132 is toward the proximal end 150.

As described above and shown in the Figures, the bidirectional barbed and beveled ports 130 positioned asymmetrically can advantageously create a helical flux that allows all ports 130 to share the same aspiration pressure. Thus, cannulas according to the present invention can be less traumatic than other multi-port harvesters, and can deliver a fine-grained, high fat content/purity yield.

In some embodiments, the cannula stem 110 may be 2.4 mm outer diameter (OD), 1.96 mm inner diameter (ID), 13 gauge, with 20 specially-configured holes 130 each having a diameter (D) of 1 mm. In other embodiments, the cannula stem 110 may be 3.0 mm OD, 2.39 mm ID, 11 gauge, with 20 specially-configured holes 130 each having a diameter (D) of 1.2 mm. The size of the cannula stem (e.g., as indicated by the OD) may vary according to the intended application. In some embodiments, for fat transfer, the OD may vary, for example, between about 2.4 mm and about 6.0 mm. The ID and the size of the holes preferably vary in proportion to the OD. The length of the cannula stem 110 may also vary according to the intended application, and in some embodiments may vary, for example, between about 10 cm and about 45 cm. In some embodiments, the length of the cannula stem 110 is about 35 cm.

In certain preferred embodiments, the cannula stem 110 comprises Type 305 stainless steel. In alternate embodiments, other suitable materials may be used. Preferably the cannula stem 110 is reusable and/or disposable.

Figure 3:
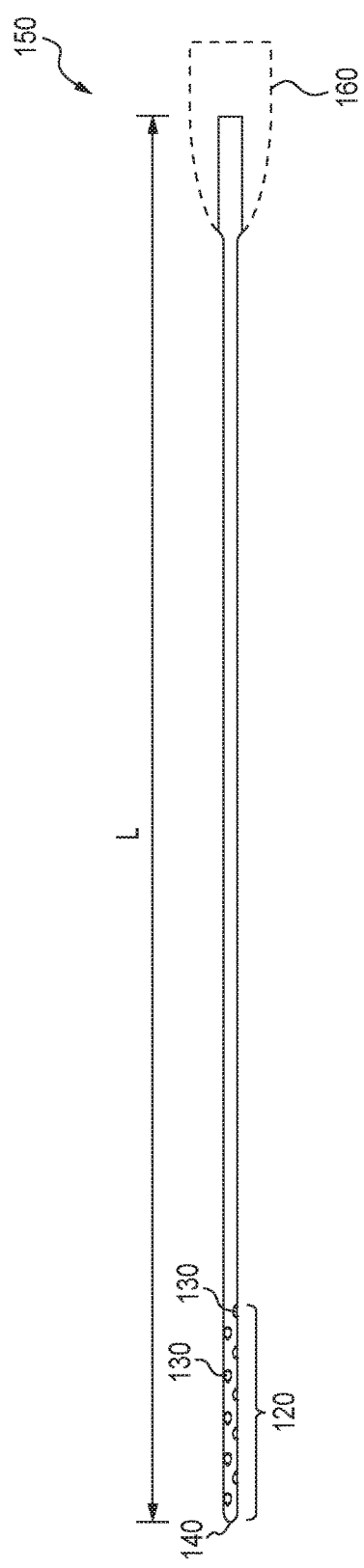
FIG. 3 shows an extended side view of a cannula according to some embodiments.

FIG. 3 shows an extended side view of a cannula 100 according to some embodiments of the invention. The proximal end 150 of the cannula (shown in FIG. 3 at right with an exemplary adapter 160 attached thereto) is preferably open and can be configured to fit any syringe connector on the market, including, but not limited to, a luer, a luer lock, a 60 cc hub, a 20 cc hub, and a super luer lock, by adding the appropriate adapter.

The following examples are given for purposes of illustration only, and are not intended to be construed in a limiting manner.

EXAMPLES

Example 1

Fat Grafting for Facial Rejuvenation in Patients with Severe Co-Morbidities

Facelift is the most effective treatment for facial rejuvenation regardless of the chosen technique. However, there are contraindications for this procedure, such as severe heart conditions, chronic obstructive pulmonary disease (COPD), heavy smoking, and any other condition adverse to several hours under anesthesia for cosmetic reasons.

Study #1: Sixty (60) patients were given a facial "thread lift" associated with fat injections in order to improve the deformities caused by residual excess skin and aging. The age range was between 62 and 73 years old. All 60 patients presented a formal indication for a facelift, but had co-morbidities or other factors that contraindicated the procedure, including heavy smoking (40+ cigarettes/day), COPD (average peak flow ≤65%), deep angiosarcoma of the temporal bone, ear prosthesis, Burkitt's lymphoma with nerve damage, and refractory heart failure (myocardial oxygen consumption MVO2=15.8 mL/minute/kg of body weight).

Study #2: Thirty-six (36) patients were given a facial "thread lift" associated with fat injections in order to improve the deformities caused by residual excess skin and aging. The age range was between 42 and 67 years old. All 36 patients presented a formal indication for a facelift, but had co-morbidities or other factors that contraindicated the procedure. 50% were heavy smokers.

In all patients, the fat was harvested using a cannula according the present invention, and processed using Puregraft filtration technology. The threads used were Silhouette Sutures, comprising a non-absorbable polypropylene strand with hollow, bio-resorbable polylactic acid (PLA) cones. The fat was typically harvested from the legs and the volume of fat transferred ranged from 10 cc to 30 cc, with an average of 20 cc per procedure. The procedures were performed under local anesthesia only.

The results of Study #1 were evaluated after six months, by comparing before and after pictures and with a satisfaction rate obtained from the patients. In all cases, a successful correction of the previous problems was achieved without any complications. Improvements were observed, for example, on the eyelid position, the jowls and mandibular lines, and all facial lines. The technique used was found to have minimal associated risks and complications and has been shown to be very effective, especially in patients that were left with no facial rejuvenation procedure as an option.

The results of Study #2 were evaluated after twelve months, by comparing before and after pictures and with a satisfaction rate obtained from the patients. In all cases, a successful correction of the previous problems was achieved without any complications. Improvements were observed, for example, on the midface and cheek region and on the eyelid position. The technique used was found to have minimal associated risks and complications and has been shown to be very effective. At twelve months, a percentage of the injected fat had been reabsorbed, but the high satisfaction rate was sustained.

Example 2

Correcting Deformities after Breast Augmentation with Silicone Implants

Breast augmentation with implants is probably the most frequently performed cosmetic surgery in the world. Unfortunately, due to the fact that breasts have a natural asymmetry and silicone implants come in pre-manufactured sizes and shapes, fine symmetry in volume and contour is often difficult to achieve. Moreover, as implants are foreign bodies, natural capsular contraction is increasingly a common complication.

Twenty-four (24) patients were given fat injections to correct deformities or asymmetries after previous breast enlargement surgery with silicone implants. Patients were divided into two groups: Group 1—Asymmetries (difference in volume; n=15) and Group 2—Deformities (difference in shape, rippling, capsular contracture, double bubble; n=9). The age range was between 19 and 32 years old. Patients were offered fat transfer to correct their problems, as opposed to breast implant replacement.

In all patients, the fat was harvested using a cannula according the present invention, and processed using Puregraft filtration technology. The fat was typically harvested from the abdominal area and the volume of fat transferred ranged from 160 cc to 360 cc, with an average of 280 cc per procedure. The fat was transferred until the desired visual result was achieved. Then, an extra 20% of the injected volume was added (over correction).

The results were evaluated after six months, by comparing before and after pictures and with a satisfaction rate obtained from the patients. In all cases, a successful correction of the previous problems was achieved without any complications. Patients' satisfaction rates after six months were "excellent" in 83.3% of cases, "good" in 12.5%, and "fair" in 4.2%. The medical team evaluation after six months rated as "excellent" in 75% of cases, "good" in 20.3%, and "fair" in 4.2%. 3D analysis showed average reabsorption to be 27.52%, which was constant and reproducible in all cases.

The medical team was highly satisfied with the technique, as it enabled them to process more fat, quicker. Patients also had the benefit of a liposculpture to harvest the fat, which may also have contributed to their satisfaction rate. Fat was found be a very powerful resource in the treatment of patients with sequelae from previous breast surgery.

Example 3

Fat Grafting with Silicone Calf Implants

Calf augmentation with sub-fascial implants is performed worldwide. Unfortunately, due to the fact that calves have a natural asymmetry and the silicone implants available for surgery have very limited options of pre-manufactured sizes and shapes (3 to 5 options only), fine symmetry in volume and contour is often difficult to achieve.

Moreover, as implants are foreign bodies and the implanted area is small, an unnatural aesthetic is not uncommon. Therefore patients with large asymmetries due, for example, to trauma, previous surgeries, or sequelae of diseases like poliomyelitis, find it impossible to match their calves with the options available in the market.

There are several general groups searching for calf augmentation surgery, including body builders (very pronounced, short and well-defined calves), female patients (seeking lean "soft" augmentation), and patients with previous scars in lower third of calves. Patients are each day more demanding concerning the final aesthetic result. However, there is a lack of calf implant sizes and shapes available in the market. Most of them are too long with a shape that is not applicable, which leads to higher complication rates and/or poor aesthetic outcomes. Thus, implants alone cannot correct all deformities.

Twenty-four (24) patients were given fat injections to correct deformities or asymmetries together with calf enlargement surgery with silicone implants. The age range was between 19 and 35 years old. All 24 patients presented either a need for aesthetic calf surgery or an asymmetry due to a previous injury/disease. Patients were divided into two groups: Group 1—Aesthetic (n=18) and Group 2—Asymmetries/Deformities (difference in shape/volume; n=6).

In all patients, the fat was harvested using a cannula according the present invention, and processed using Puregraft filtration technology. The fat was typically harvested from the abdominal area and the volume of fat transferred ranged from 60 cc to 160 cc, with an average of 120 cc per procedure. An anatomical plane facilitates fat transfer on top of sub-fascial implants.

The results were evaluated after six months, by comparing before and after pictures and with a satisfaction rate obtained from the patients. In all cases, a successful correction of the previous problems was achieved without any complications. This technique has minimal associated risks and complications, and has been shown to be very effective. The medical team was highly satisfied with the technique, as it enabled them to process more fat, quicker. At six months, a percentage of the injected fat had been reabsorbed, but the high satisfaction rate was sustained.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

What is claimed is:

1. A harvesting cannula comprising a hollow elongated stem, an open proximal end, and a closed distal end, wherein a distal portion of the stem comprises a plurality of barbed and beveled ports, each port comprising a substantially circular hole having a diameter (D) of at least about 1 mm parallel to a longitudinal axis of the cannula, each hole having a beveled portion at one end and an elevated barbed portion opposite thereto, wherein each beveled portion has a substantially triangular shape.

2. The harvesting cannula of claim 1, wherein each beveled portion comprises a 60 degree machined cutting edge.

3. The harvesting cannula of claim 1, wherein each hole has a diameter (D) of about 1 mm.

4. The harvesting cannula of claim 1, wherein each hole has a diameter (D) of about 1.2 mm.

5. The harvesting cannula of claim 1, wherein the barbed and beveled ports are distributed in lines along the distal portion of the stem, each line staggered and inverted in orientation relative to the lines adjacent thereto.

6. The harvesting cannula of claim 5, wherein the barbed and beveled ports are distributed in four lines of five ports each.

7. The harvesting cannula of claim 5, each line having an identical line opposite thereto, whereby holes on opposite sides of the stem are aligned and provide a clear opening through the stem.

8. The harvesting cannula of claim 1, wherein the stem has a length (L) of about 10 cm to about 45 cm.

9. The harvesting cannula of claim 1, wherein the stem has a length (L) up to about 35 cm.

10. The harvesting cannula of claim 1, wherein the stem is 13 gauge with an outer diameter (OD) of about 2.4 mm and an inner diameter (ID) of about 1.96 mm.

11. The harvesting cannula of claim 1, wherein the stem is 11 gauge with an outer diameter (OD) of about 3.0 mm and an inner diameter (ID) of about 2.39 mm.

12. The harvesting cannula of claim 1, wherein the stem has an outer diameter (OD) of about 2.4 mm to about 6.0 mm.

13. The harvesting cannula of claim 1, wherein each elevated barbed portion has an extension (E) of about 1 mm beyond an outer surface of the stem.

14. A harvesting cannula comprising a hollow elongated stem, an open proximal end, and a closed distal end, wherein a distal portion of the stem comprises a plurality of barbed and beveled ports, each port comprising a substantially circular hole having a diameter (D) of at least about 1 mm parallel to a longitudinal axis of the cannula, each hole having a beveled portion at one end and an elevated barbed portion opposite thereto, wherein each elevated barbed portion has an extension (E) of about 1 mm beyond an outer surface of the stem.

15. The harvesting cannula of claim 14, wherein each beveled portion comprises a 60 degree machined cutting edge.

16. The harvesting cannula of claim 14, wherein the stem has a length (L) of about 10 cm to about 45 cm.

17. The harvesting cannula of claim 14, wherein the stem has an outer diameter (OD) of about 2.4 mm to about 6.0 mm.

18. A harvesting cannula comprising a hollow elongated stem, an open proximal end, and a closed distal end, wherein a distal portion of the stem comprises a plurality of barbed and beveled ports, each port comprising a substantially circular hole having a diameter (D) of about 1 mm to about 1.2 mm parallel to a longitudinal axis of the cannula, each hole having a beveled portion at one end and an elevated barbed portion opposite thereto, wherein each beveled portion has a substantially triangular shape.

* * * * *